United States Patent
Shelley, Jr. et al.

(10) Patent No.: US 9,903,809 B2
(45) Date of Patent: Feb. 27, 2018

(54) SYSTEM FOR MEASURING THERMAL DEGRADATION OF COMPOSITES AND METHOD OF MAKING AND USING

(71) Applicant: The Boeing Company, Chicago, IL (US)

(72) Inventors: Paul H. Shelley, Jr., Lakewood, WA (US); Gregory J. Werner, Lacey, WA (US); Milan Milosevic, Westport, CT (US); Paul Vahey, Seattle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 15/696,701

(22) Filed: Sep. 6, 2017

(65) Prior Publication Data

US 2017/0370846 A1   Dec. 28, 2017

Related U.S. Application Data

(63) Continuation-in-part of application No. 14/855,892, filed on Sep. 16, 2015, now Pat. No. 9,791,365.

(51) Int. Cl.
    *G01N 21/27*   (2006.01)

(52) U.S. Cl.
    CPC ................... *G01N 21/27* (2013.01)

(58) Field of Classification Search
    CPC ..... G01N 21/27; G01N 21/33; G01N 21/6465
    See application file for complete search history.

(56) References Cited

U.S. PATENT DOCUMENTS

| 3,244,073 A * | 4/1966 | Bouwers ............. G02B 17/008 |
| | | 359/727 |
| 6,903,339 B2 | 6/2005 | Shelley et al. |
| 2005/0067569 A1* | 3/2005 | Shelley ............. G01N 21/3563 |
| | | 250/341.8 |

(Continued)

FOREIGN PATENT DOCUMENTS

| EP | 0 267 766 | 5/1988 |
| EP | 2 778 661 | 9/2014 |
| WO | 2014/032744 | 3/2014 |

OTHER PUBLICATIONS

EP, Extended European Search Report and Opinion; European Patent Application No. 16186421.0, 10 pages. (dated Jan. 25, 2017).

(Continued)

*Primary Examiner* — Casey Bryant
(74) *Attorney, Agent, or Firm* — Thompson Hine LLP

(57) ABSTRACT

A system for measuring thermal degradation of composites includes a cylindrical body; a bottom cover having a lower central aperture; an upper concave mirror facing the bottom cover with an upper central orifice concentric with a central axis of the body; a lower concave mirror facing the upper concave mirror with a lower central orifice concentric with the central axis; a source of actinic radiation between the upper concave mirror and the lower concave mirror on the central axis to direct actinic radiation through the lower central orifice and lower central aperture; and a camera with an image sensor positioned concentrically relative to the upper central orifice; wherein the bottom cover is adjustable relative to the cylindrical body to provide a focusing function for the image sensor by varying the distance from the lower central orifice and the upper reflective surface.

20 Claims, 3 Drawing Sheets

(56) References Cited

U.S. PATENT DOCUMENTS

2014/0273240 A1* 9/2014 Georgeson .......... G01N 31/229
436/7

OTHER PUBLICATIONS

Fisher, W. G. et al., "Nondestructive Inspection of Graphite-Epoxy Composites for Heat Damage Using Laser-Induced Fluorescence"; Applied Spectroscopy; The Society for Applied Spectroscopy; vol. 49, No. 9, XP000524517; pp. 1225-1231 (Sep. 1, 1995).
US, Non-Final Office Action, U.S. Appl. No. 14/855,892, 12 pages. (dated Nov. 22, 2016).
US, Final Office Action, U.S. Appl. No. 14/855,892, 13 pages. (dated Mar. 17, 2017).
US, Notice of Allowance, U.S. Appl. No. 14/855,892, 8 pages. (dated Jun. 6, 2017).

* cited by examiner

SYSTEM FOR MEASURING THERMAL DEGRADATION OF COMPOSITES AND METHOD OF MAKING AND USING

TECHNICAL FIELD

This disclosure relates to systems for non-destructive testing of materials and, more particularly, to systems for detecting and measuring thermal degradation of composite materials, and methods of making and using such systems.

BACKGROUND

The structural components of vehicles, such as aircraft, are comprised of increasing amounts of composite materials, such as carbon fiber reinforced plastic (CFRP). Heat damage to such composite materials may occur from a number of causes, including a lightning strike, an electrical short in wiring, or an overheated component. When heated to an elevated temperature for an extended period of time, composite materials may lose some of their desirable mechanical properties. In particular, such heating may reduce the ability of the composite materials to withstand mechanical stresses.

Currently, non-destructive testing of composite materials is performed with a portable FTIR (Fourier Transform Infrared) spectrometer to identify any potential degradation. An FTIR spectrometer uses the selective IR (infrared) absorbance of different chemical compounds, so that oxidized carbon is easily distinguished from unoxidized material. The relatively grainy consistency of the composite material leads to results that may be highly variable on a scale of the inspection area, which typically is 1 mm in diameter. This requires measurements to be made on a statistically significant number of different nearby spots in order to reach a reliable conclusion on the degree of damage.

Such FTIR spectrometers are relatively large and expensive. Further, their size does not lend their use to inspection of composite materials in difficult-to-reach areas. Accordingly, there is a need for a small, portable, and inexpensive system for measuring thermal degradation of composites.

SUMMARY

This disclosure is directed to a system and method for measuring thermal degradation of composites that utilizes a small, hand-held detection probe that is relatively inexpensive to manufacture and operate. In one embodiment, the probe includes a cylindrical body having a top opening, a bottom opening, and a central axis; a bottom cover enclosing the bottom opening and including a lower central aperture concentric with the central axis; an upper mirror mounted in the cylindrical body and facing the bottom cover, the upper mirror having an upper concave reflective surface and an upper central orifice concentric with the central axis; a lower mirror mounted in the cylindrical body and facing the upper concave reflective surface, the lower mirror having a lower concave reflective surface and a lower central orifice concentric with the central axis; a source of actinic radiation positioned within the cylindrical body between the upper mirror and the lower mirror on the central axis to direct actinic radiation along the central axis through the lower central orifice and the lower central aperture to a test area visible through the lower central aperture; and a camera mounted on the cylindrical body and having an image sensor positioned concentrically relative to the upper central orifice to receive radiation emitted from the test area; wherein the bottom cover is adjustable relative to the cylindrical body to provide a focusing function to the emitted radiation reflected from the lower reflective surface received by the image sensor by varying a distance from the lower central orifice and the upper reflective surface.

In another embodiment, a system for measuring thermal degradation of composites includes a probe having a cylindrical body with a top opening, a bottom opening, and a central axis; a bottom cover enclosing the bottom opening and including a lower central aperture concentric with the central axis; an upper concave mirror mounted in the cylindrical body and facing the bottom cover, the upper concave mirror having an upper reflective surface and an upper central orifice concentric with the central axis; a lower concave mirror mounted in the cylindrical body and facing the upper concave mirror, the lower concave mirror having a lower reflective surface and a lower central orifice concentric with the central axis; a source of actinic radiation positioned within the cylindrical body between the upper concave mirror and the lower concave mirror on the central axis and positioned to direct actinic radiation along the central axis through the lower central orifice and the lower central aperture; and a camera mounted on the cylindrical body and having an image sensor positioned concentrically relative to the upper central orifice. A display is connected to the camera for displaying an image of radiation emitted from a test area exposed to the actinic radiation and collected by the image sensor. The bottom cover is adjustable relative to the cylindrical body to provide a focusing function to the image on the display.

In yet another embodiment, a method for making a probe for use in measuring thermal degradation of composites includes mounting a source of actinic radiation within a cylindrical body, the cylindrical body having a bottom opening and a central axis; attaching a lower concave mirror to the cylindrical body, the lower concave mirror having a lower reflective surface facing the source of actinic radiation and a lower central orifice concentric with the central axis; mounting an upper concave mirror in the cylindrical body, the upper concave mirror having an upper reflective surface facing the lower reflective surface and the source of actinic radiation, the upper concave mirror having an upper central orifice concentric with the central axis, such that the source of actinic radiation is between the upper concave mirror and the lower concave mirror on the central axis and positioned to direct actinic radiation along the central axis through the lower central orifice; mounting a camera on the cylindrical body, the camera having an image sensor positioned concentrically relative to the upper central orifice; and attaching a bottom cover to the cylindrical body, the bottom cover enclosing the bottom opening and including a lower central aperture concentric with the central axis. The bottom cover is adjustable relative to the cylindrical body to provide a focusing function to the emitted radiation received by the image sensor by varying a distance from the lower central orifice and the upper reflective surface.

Other objects and advantages of the disclosed system for measuring thermal degradation of composites and the method of making and using it will be apparent from the following description, the accompanying drawings, and the appended claims.

DETAILED DESCRIPTION

Figure 1:
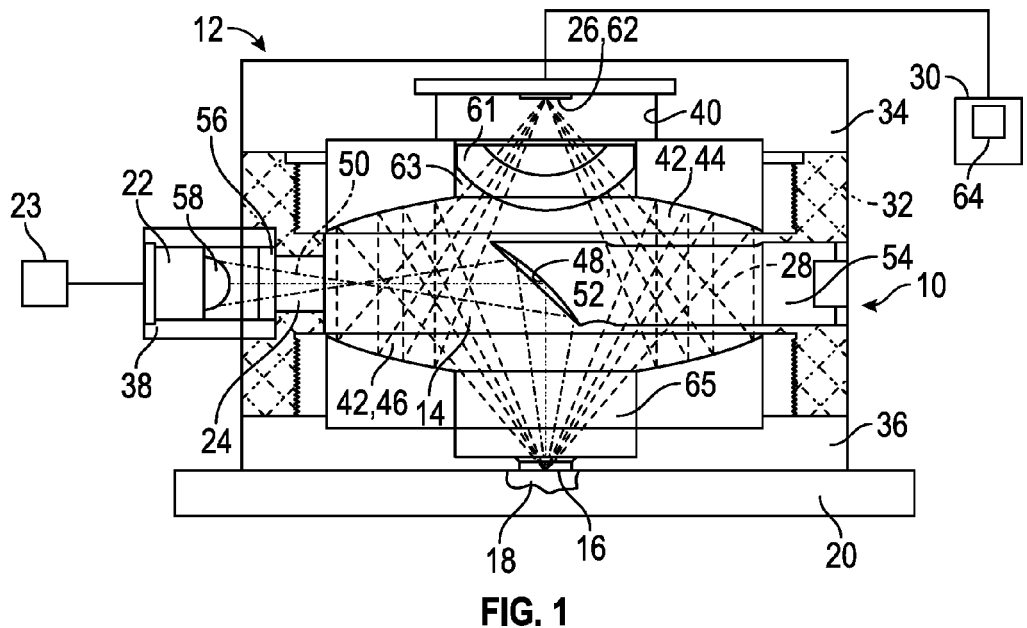
FIG. 1 is a schematic side elevation in section of an embodiment of the system for measuring thermal degradation of composites.

As shown in FIG. 1, a system for measuring thermal degradation of composites, generally designated 10, may include a housing 12 forming an interior 14 with an opening 16 shaped to expose a test area 18 of a composite, or segment of composite, 20 to be tested. A light-emitting diode (LED) 22 may be powered by a power supply 23 and emits ultraviolet (UV) radiation, or emits primarily UV radiation. The LED 22 may be mounted on the housing 12 and oriented to direct UV radiation into the interior 14 through a side opening 24 to direct the UV radiation to the opening 16. An image sensor 26 is mounted on the housing 12 and open to the interior 14 to receive radiation 28 emitted from the test area 18 passing through the opening 16 into the interior 14. An image processor 30 may be connected to receive a signal from the image sensor 26. As will be described in detail below, the image processor 30 may determine a presence or absence of thermal degradation of the test area 18 in response to the signal from the image sensor 26.

In an embodiment, the housing 12 may include a side wall 32, an upper wall 34 attached to the side wall, and a lower wall 36 attached to the side wall. The side wall 32 may be generally cylindrical in shape, and the upper wall 34 and lower wall 36 may be disk shaped, matching the side wall in diameter. The side wall 32 may include the side opening 24 that receives the LED 22. The side wall 32, the upper wall 34, and the lower wall 36 may combine to define the interior 14 of the housing 12. The LED 22 may be mounted within a housing 38 that is attached or mounted on the side wall 32. The image sensor 26 may be mounted in a recess 40 formed in the upper wall 34. The opening 16 may be formed in the lower wall 36.

In an embodiment, the housing 12 may include a first reflective surface 42 positioned in the interior 14. The first reflective surface 42 may be shaped and positioned to receive the radiation 28 emitted from the test area 18, and reflect the radiation emitted or fluoresced from the test area to the image sensor 26. Also in the embodiment, the first reflective surface 42 may include a first parabolic mirror 44, which in embodiments is a disk-shaped paraboloid, mounted on the upper wall 34, and a second parabolic mirror 46, which in embodiments is a disk-shaped paraboloid, mounted on the lower wall 36. The first and second parabolic mirrors 44, 46 may be shaped and positioned such that the first parabolic mirror receives the radiation 28 emitted or fluoresced from the test area 18 and reflects the radiation emitted from the test area to the second parabolic mirror 46. The second parabolic mirror may be shaped and positioned to reflect the radiation 28 emitted from the test area 18 and reflected from the first parabolic mirror 44 to the image sensor 26. In an embodiment, the first and second parabolic mirrors 44, 46 may face each other, and in still other embodiments, may lie on a common central axis and be parallel to each other.

The system 10 may include a second reflective surface 48 mounted in the interior 14 of the housing 12 and positioned to receive the UV radiation 50 from the LED 22. The second reflective surface 48 may be positioned to reflect the UV radiation 50 the opening 16 in the housing 12, where it impinges on the test area 18 of the composite 20 to be tested. In an embodiment, the second reflective surface 48 may include an ellipsoid mirror 52. The ellipsoid mirror 52 may be attached to or mounted on a holder 54 that, in turn, may be attached to the side wall 32 of the housing 12. Also in an embodiment, the second reflective surface 48, ellipsoid mirror 52 and holder 54 may be positioned between the first and second parabolic mirrors 44, 46, respectively, within the interior 14 of the housing 12.

The system 10 also may include a high-pass filter 56 that may be mounted in the housing 12, and in particular in the opening 24 in the side wall 32. The high-pass filter 56 may be selected to permit only the UV component of the primarily UV radiation 50 from the LED 22 to pass through the high-pass filter and enter the interior 14 of the housing 12. The LED 22 may include an integral ball lens 58 shaped and positioned to focus the primarily UV radiation 50 emitted by the LED 22. The primarily UV radiation 50 may be focused by the ball lens 58 into the first focal point of the ellipsoid mirror 52, where it may be reflected through the opening 16 in the bottom wall 36 into the second focal point of the ellipsoid mirror, into which the test area 18 of the composite 20 to be tested is placed.

The system 10 may include a UV-blocking filter 61 that is selected to allow visible light radiation 28 to pass, but block UV radiation. The UV-blocking filter 61 may be mounted on the housing 12 such that only emitted visible light radiation 28 reaches the image sensor 26 from the interior 14 of the housing. In an embodiment, the first parabolic mirror 44 may include a circular recess 63, and the UV-blocking filter 61 may be shaped to fit within the recess immediately adjacent the image sensor 26. In an embodiment, the image sensor 26 may be a digital camera 62. Similarly, in an embodiment, the second parabolic mirror 46 may include a circular passage 65 that connects the opening 16 with the interior 14 of the housing 12.

Also in an embodiment, the image processor 30 may be selected from, or operated by software loaded in, a laptop computer and a mobile device, such as a handheld tablet computer. In embodiments, the laptop computer or mobile device also may contain the power supply 23 for the LED (FIG. 1). The connection between the image sensor 26 and the image processor 30 may be hard wired or wireless. The image processor 30 may be programmed to compare a ratio of color intensities of the radiation 28 emitted from the test area 18 of two colors selected from red and green, red and blue, and blue and green. The image processor 30 may include a display 64 that indicates the presence or the absence of thermal degradation of the test area 18, dependent upon the comparison of the ratios to the stored values.

The system 10 may operate by energizing the ultraviolet LED 22, which emits UV radiation 50 through high-pass filter 56 into the interior 14 of the housing 12. The UV radiation 50 is reflected by the ellipsoid mirror 52 downwardly through the circular passage 65 and opening 16, where it contacts the test area 18 of the composite material 20. This irradiation may cause the composite material 20 in the test area 18 to fluoresce in the visible light range, emitting radiation 28 in the visible light range that is reflected by the first parabolic reflector 44 to the second parabolic reflector 46, and from the second parabolic reflector 46 upwardly through the UV-blocking filter 61 to the image sensor 26. The pixels of the image sensor 26, which may be a digital camera 62, receive the visible light radiation 28 fluoresced from the test area 18.

Figure 3A:
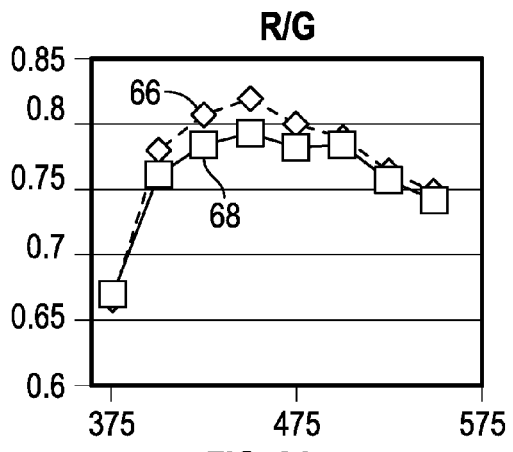
FIGS. 3A, 3B, and 3C are graphs of the ratio of intensity of fluoresced radiation versus exposed temperature of a first side of actual test specimens of composite material in which data points are ratios of intensities of the red to green, red to blue, and blue to green segments of the visible light spectrum, using two methods of calculating ratios.
Figure 3B:
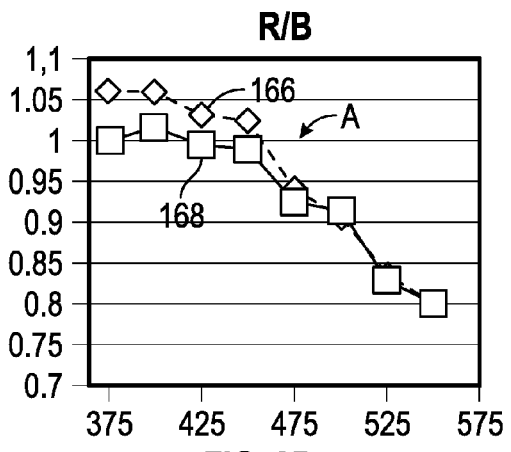
Figure 3C:
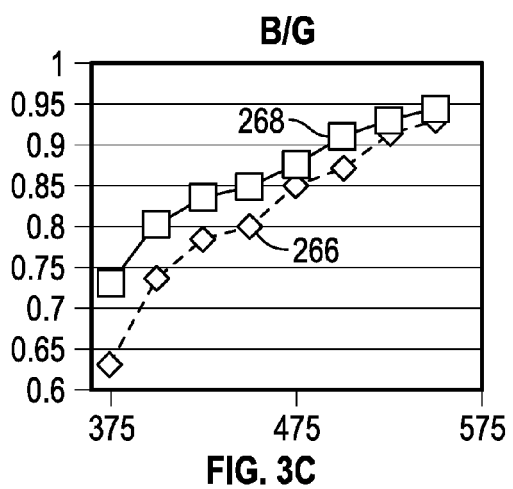
Figure 4A:
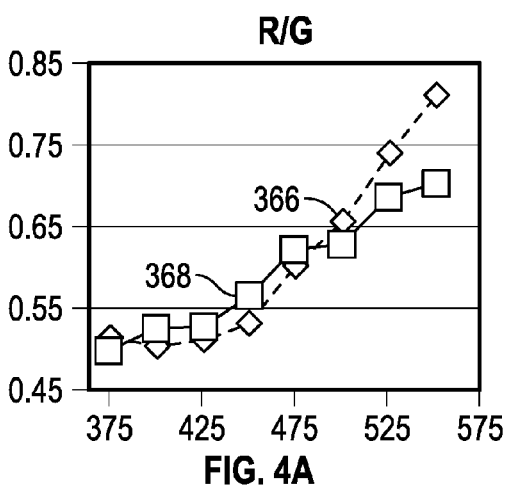
FIGS. 4A, 4B, and 4C are graphs of the ratio of intensity of fluoresced radiation versus exposed temperature of a second, opposite side of the actual test specimens of composite material in which data points are ratios of intensities of the red to green, red to blue, and blue to green segments of the visible light spectrum, using two methods of calculating ratios.
Figure 4B:
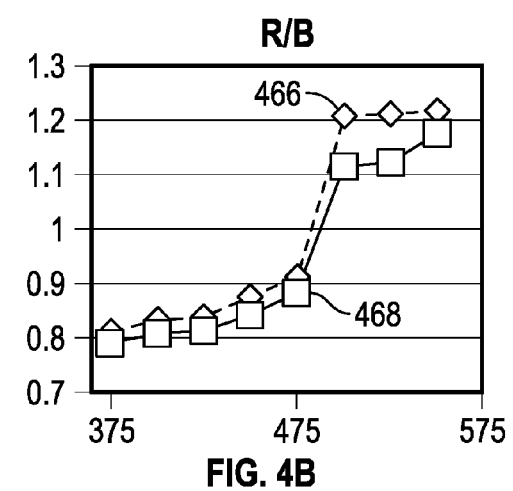
Figure 4C:
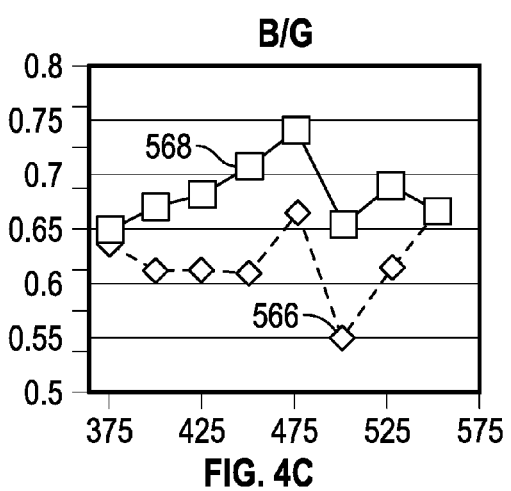

FIGS. 3A, 3B, and 3C, and 4A, 4B, and 4C show the results of tests of the disclosed system 10, measuring the intensity of the radiation 28 received by the image sensor 26, which in the test was a digital camera 62, for different colors of the visible light radiation 28 for 8 different specimens of composite carbon fiber reinforced plastic material, each of which would represent test area 18 (FIG. 1). FIGS. 3A-3C are the results taken of a first side taken at 4 random points on each of the 8 specimens, and FIGS. 4A-4C are the results taken of the second or opposite side of the same 8 specimens taken at 4 random points each. Each of the 8 specimens was heated to a different temperature for the same one-hour time interval. The temperatures at which the 8 specimens were heated ranged from 375° F. to 550° F. in 25° F. increments.

The intensity of color fluorescing from a test specimen of composite material using the disclosed system 10 may vary with the temperature and the duration of thermal exposure of the test specimen. FIGS. 3A-3C and 4A-4C each show an image file created by the image processor 30 from a signal received by the image sensor 26 that may be converted by a software in the image processor into three matrices: red, green, and blue, where each matrix element may display the intensity of a particular pixel for red, green, and blue color. In order to avoid alignment and excitation light variability, the ratios of red/green, red/blue, and blue/green were calculated, thus making the ratios insensitive to alignment, intensity of the light-emitting diode 22, gain, or exposure times used by the camera 62. On the x or horizontal axis of each graph, the temperature of a side of the test specimen of composite material, representing test area 18, is plotted. On the y or vertical axis, the ratio of intensities of the colors is indicated for that temperature. The camera 62 may read some intensity even when the LED 22 is turned off. In such case, that intensity is measured and subtracted from the readings made when the LED is turned on.

In FIG. 3A, the small, diamond-shaped data points 66 connected by the broken line represent the ratio of red visible light intensity to green visible light intensity from the 8 test specimens after exposures to 375° F., 400° F., 425° F., 450° F., 475° F., 500° F., 525° F., and 550° F. for one hour. The data points represented by the small, diamond-shaped data points 66 are calculated using a first method, by ratioing the intensities pixel-by-pixel, and then calculating the average ratio over the entire digital camera image. The data points represented by the larger squares 68 in FIG. 3A connected by a solid line represent the ratio of red visible light intensity to green visible light intensity for the same temperatures and time interval of the 8 specimens, using a second method in which the ratio was calculated by first taking the average of the color intensity over all the pixels of the digital camera 62 for red visible light and for green visible light, and then calculating the ratio of the two average values.

In FIG. 3B, data points are plotted for the same temperature values for ratios of red visible light intensity versus blue visible light intensity. Small, diamond-shaped data points 166 represent the ratio of red to blue intensity using the first method of ratioing the intensities pixel-by-pixel, then calculating the average ratio over the entire digital camera image, and the large squares 168 represent the ration of red to blue intensity using the second method of taking the average of the color intensity over all the pixels for red to blue, then calculating the ration of the two average values, for each of the 8 specimens heated to the temperatures ranging from 375° F. to 550° F. in 25° F. increments. Similarly, FIG. 3C shows data points plotted for blue to green intensity for the 8 samples using the first ratioing method, represented by small diamonds 266, and using the second ratioing method, represented by large squares 268. FIG. 4A shows data points plotted for red to green intensity for the second or opposite sides of the 8 samples using the first ratioing method, represented by small diamonds 366, and large squares 368, using the second ratioing method. FIG. 4B shows data points plotted for red to blue intensity for the second or opposite sides of the 8 samples using the first ratioing method, represented by small diamonds 466, and large squares 468, using the second ratioing method; and FIG. 4C shows data points plotted for blue to green intensity for the second or opposite sides of the 8 samples using the first ratioing method, represented by small diamonds 566, and large squares 568, using the second ratioing method.

Useful data may be obtained from those of the graphs that show a continuous increase or decrease with temperature. Accordingly, the graphs of FIGS. 3B and 4B may be the most useful for determining whether the particular composite material 20 being measured has been damaged or degraded by heating. With respect to FIG. 3B, there is a noticeable decrease in intensity at a temperature at approximately 450° F. on the x axis at A. Similarly, in FIG. 4B, there is a noticeable increase in intensity that begins at about 450° F. on the x axis. That temperature and time interval may be considered significant for effecting thermal degradation of a composite material. Accordingly, such ratio values may be stored in the image processor 30, and compared with a test made of the test area 18. By measuring the intensities and calculating the aforementioned ratios, the exposure temperature may be back calculated by the image processor 30 (FIG. 1). Other types of composite materials, which may degrade at different time-temperature combinations, and be indicated by different ratios, may be stored in image processor 30 as well.

Figure 2:
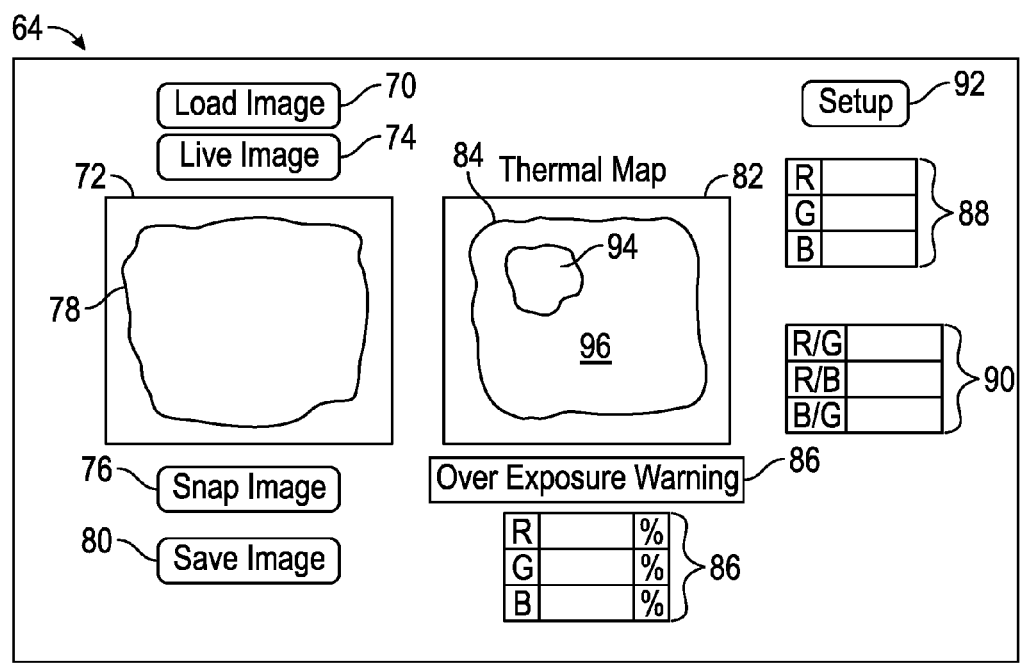
FIG. 2 is a schematic representation of a display of data received by the systems of FIGS. 1 and 5.

As shown in FIG. 2, a display 64 may include the screen illustrated in the figure, either as hardware or as a virtual screen on a computer display screen, and appropriate software to operate it. The display 64 may include a touch screen or virtual button 70, marked "LOAD IMAGE" for loading a previously saved image into the left frame 72. The virtual or actual button 74 marked "LIVE IMAGE" may switch the left frame 72 to the live image from the image sensor 26 mounted in the housing 12. The actual or virtual button 76 marked "SNAP IMAGE" actuates the image sensor 26 to take a snapshot from a live image of the test area 18 and place it into the left frame 72. In FIG. 2, the image 78 shown in the left frame may be such a live image. The actual or virtual button 80 marked "SAVE IMAGE" may be actuated to save the snapped image 78 to a disc or other non-volatile storage or memory.

The right frame 82 of the display 64 may display the processed image 84, which may take the form of a thermal map of the snapped or loaded, but not of the live, image. The display 64 also may include an analog-to-digital saturation or overexposure warning 86 that may indicate the percent of the over exposed pixels for red, green, and blue, separately. The red, blue, and green text boxes 88 may display an average value of red, green, and blue color in the snapped and loaded image, and boxes 90 may display the ratios of red to green, red to blue, and blue to green and display the corresponding ratios. The virtual or actual button 92 marked "SETUP" may open a setup window with access to camera settings for the image sensor 26, save to folder selection and other features of the display 64. The thermal map 82 may use the developed model to assign and color code the temperature of each pixel.

Accordingly, in embodiments, the display 64 may indicate thermal degradation by appropriate color coding of the image 84 on the thermal map 82 if the ratio of either red/green, red/blue, or blue/green is selected from less than a stored value, or greater than a stored value. In an embodiment, the display 64 may activate a first indicator, such as a color 94 area, if the image processor 26 detects thermal degradation of the test area 18, and the display 64 may activate a second indicator 96 if the image processor does not detect thermal degradation in a portion of the test area. In embodiments, the image processor 26 may assign a first color 96 to an area of no thermal degradation, and a second color 94 to an area of thermal degradation in the test area 18. As shown in FIG. 2, the display 64 may display in window 82 a composite image of the test area 18 in which areas of no thermal degradation 96 are colored with a first color, and areas of thermal degradation 94 are colored with a second color.

A method embodied in the system 10 for measuring thermal degradation of composites may include actuating the LED 22 to emit primarily UV radiation 50 into an interior 14 of the housing 12. The UV radiation 50 may be directed by the ellipsoid mirror 52 from the interior 14 of the housing 12 through the opening 16 in the housing to a test area 18 of the material composite 20 to be tested. This UV radiation may cause the composite material 20 to fluoresce visible light radiation 28. The visible light radiation 28 may be reflected first from the first parabolic mirror 44 to the second parabolic mirror 46, and from the second parabolic mirror through the UV filter 61 to the image sensor 26. The image sensor 26 detects the visible light radiation and generates a signal corresponding to the intensity of the radiation in the colors red, blue, and green. This signal may be processed by the image processor 30 to a display 64 that indicates a presence or absence of thermal degradation of the test area 18 of the composite 20.

The system 10 and method for measuring thermal degradation of composites described herein may be provided in a housing 12 that is small and handheld. The image processor 30 likewise may be compact and portable, and may be in the form of a laptop, handheld device, or tablet. The display 64 may provide a rapid and easily discernible indication of the presence of thermal degradation of a composite material 20.

Figure 5:
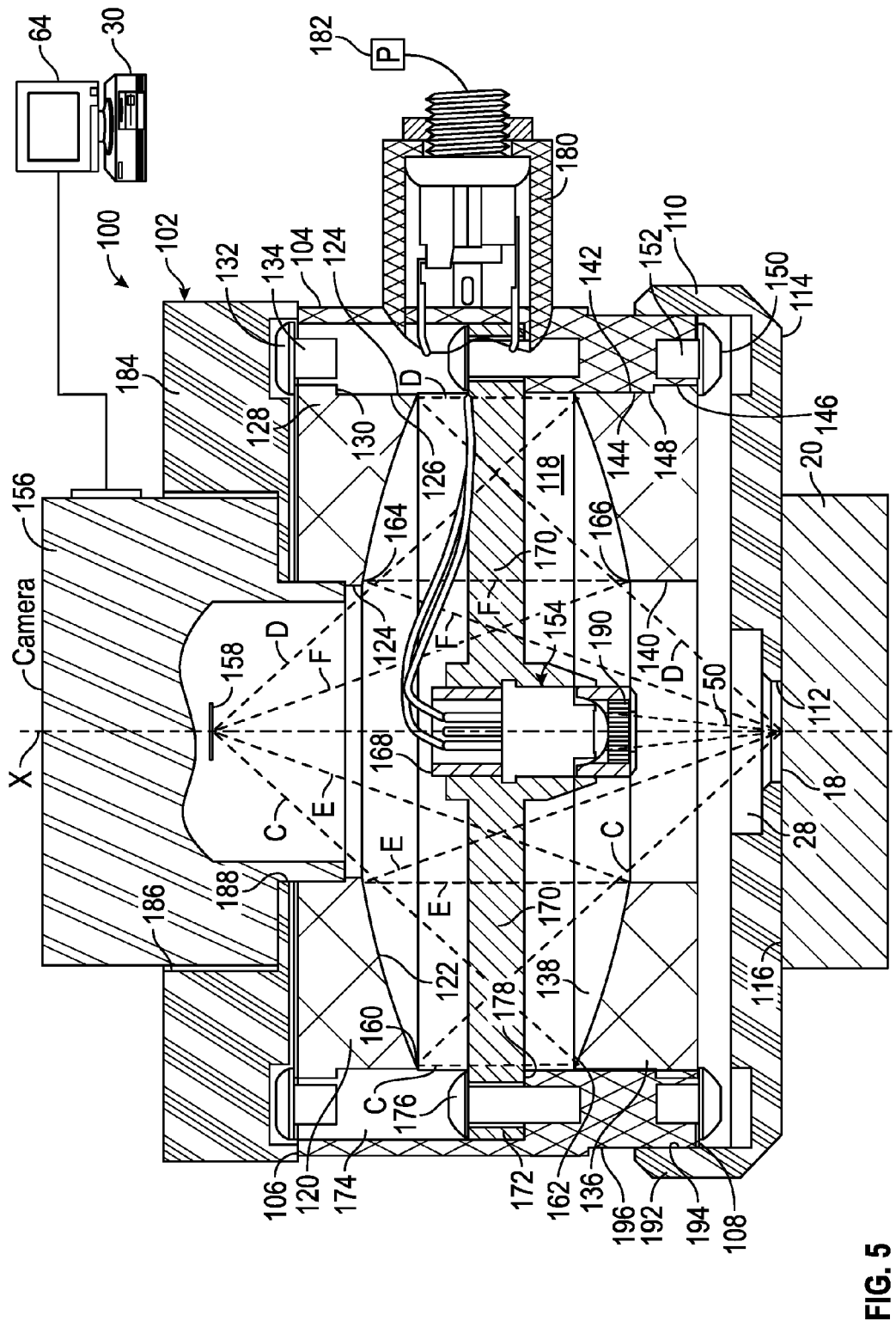
FIG. 5 is a schematic side elevation in section of another embodiment of the disclosed system for measuring thermal degradation of composites.

As shown in FIG. 5, in another embodiment, a system 100 for measuring thermal degradation of composites may be provided that is likewise small and handheld. System 100 includes a probe 102 for use in measuring thermal degradation of composites, such as composite 20, which may be CFRP. The probe 102 may include a cylindrical body 104 having a top opening 106, a bottom opening 108, and a central axis X. The cylindrical body 104 may take the form of a cylinder that is round in cross section (i.e., viewed in a plane perpendicular to central axis X). In other exemplary embodiments, the cylindrical body 104 may be polygonal in cross section. The central axis X passes through the center of the cylindrical body 104 when viewed in the direction of the central axis.

A bottom cover 110 encloses the bottom opening 108 and includes a lower central aperture 112 therethrough concentric with the central axis X. In exemplary embodiments, the bottom cover 110 has a flat or substantially flat underside 114 so that the probe can lie flat against the flat upper surface 116 of the section of composite 20 to be measured. As shown in FIG. 5, the lower central aperture 112 exposes the test area 18 of the composite 20 to the interior 118 of the probe 102. In an exemplary embodiment, the bottom cover 110 is made of a plastic, such as nylon, CFRP, or another material that does not scratch or damage the composite 20 being measured.

An upper mirror 120 is mounted in the cylindrical body 104 and faces the bottom cover 110. The upper mirror 120 has an upper concave reflective surface 122, which in embodiments is a disk-shaped paraboloid, and an upper central orifice 124 concentric with the central axis X. In an exemplary embodiment, the upper mirror 120 includes a radial exterior surface 124 shaped to fit against an adjacent interior wall 126 of the cylindrical body 104, and includes an upper peripheral projecting rim 128. The rim 128 is seated against a complementarily shaped shoulder 130 countersunk into the top opening 106. The upper mirror 120 is held in place within the cylindrical body 104 by the heads 132 of a plurality of screws 134 threaded into the top opening 106.

Similarly, a lower mirror 136 is mounted in the cylindrical body 104 and faces the upper concave reflective surface 122. The lower mirror 136 has a lower concave reflective surface 138, which in embodiments is a disk-shaped paraboloid, and a lower central orifice 140 concentric with the central axis X. In an exemplary embodiment, the lower mirror 136 includes a radial exterior surface 142 shaped to fit against an adjacent interior wall 144, which may or may not have the same shape as surface 124, of the cylindrical body 104. The radial exterior surface 142 includes a lower peripheral projecting rim 146. The rim 146 is seated against a complementarily shaped shoulder 148 countersunk into the bottom opening 108. The lower mirror 136 is held in place within the cylindrical body 104 by the heads 150 of a plurality of screws 152 threaded into the bottom opening 108.

A source of actinic radiation 154 is positioned within the cylindrical body 104 between the upper mirror 120 and the lower mirror 136 and is concentric with the central axis X to direct actinic radiation along the central axis through the lower central orifice 140 and the lower central aperture 112 to the test 18 area visible through the lower central aperture. In an exemplary embodiment, the source of actinic radiation 14 includes a focusing lens, such as a ball lens, to direct actinic radiation along axis X. A camera 156 is mounted on the cylindrical body 104 and has an image sensor 158 positioned concentrically relative to the upper central orifice 124 to receive radiation emitted from the test area 18 in response to exposure to the actinic radiation from the source 154.

In exemplary embodiments, the bottom cover 110 is adjustable relative to the cylindrical body 104 to provide a focusing function to the emitted radiation reflected from the lower reflective surface 138 received by the image sensor 158. In embodiments, the bottom cover 110 is cup shaped and includes an upstanding collar 192 with a threaded inner surface 194 that engages a corresponding cylindrical threaded lower portion 196 of the outer surface of the cylindrical body 104. Rotation of the lower bottom cover 110 relative to the lower portion 196 of the cylindrical body 104 varies the distance from the lower central orifice 112

(and hence from the upper surface 116 of the test area 18) to the upper reflective surface 122.

By varying this distance, the length of the path of emitted or fluoresced radiation, which in embodiments is visible light, from the test area 18 of the upper surface 116 to the image sensor 158 is varied, thus providing the focusing function of the probe 102. As shown in FIG. 5, a distance is selected so that at the focal point of the upper reflective surface 122 is on the upper surface 116 of the test area 18. Since in use the underside 114 of the bottom cover 110 rests upon the upper surface 16 of the composite 20, movement of the cover 114 toward and away from the cylindrical body 104 also moves the test area 18 toward and away from the cylindrical body, which varies the length of the rays of radiation emitted from the test area 18 to the image sensor 158 of the camera 156.

In exemplary embodiments, the upper reflective surface 122 and the lower reflective surface 138 are coaxial with each other and with the cylindrical probe body 104 at the central axis X. Further, in embodiments, the upper reflective surface 122 and the lower reflective surface 138 have identical paraboloid curvatures, and the upper central orifice 124 and the lower central orifice 140 are equal in diameter and also are coaxial with each other and with the central axis X.

In an exemplary embodiment, the source 154 of actinic radiation is positioned within the cylindrical body 104 between the upper reflective surface 122 and the lower reflective surface 138 in a location that does not block emitted radiation from the source of actinic radiation that is emitted from the test area 18 through the central aperture to the upper reflective surface. In another embodiment, the source 154 of actinic radiation is also positioned within the cylindrical body 104 between the upper reflective surface 122 and the lower reflective surface 138 in a location that does not block emitted radiation from the source of actinic radiation that is reflected from the lower reflective surface to the image sensor 158. In yet another embodiment, the source 154 of actinic radiation is positioned within the cylindrical body 104 between the upper reflective surface 122 and the lower reflective surface 138 in a location that does not block emitted radiation from the source of actinic radiation that is reflected through the central aperture 112 to the upper reflective surface, and that does not block emitted radiation from the source of actinic radiation that is reflected from the lower reflective surface to the image sensor 158.

The lower central orifice 112 is shaped such that a maximum angle of emitted radiation from the test area passing therethrough, represented by rays C and D, contacts an outermost periphery 160 of the upper reflective surface 122, and is reflected to an outermost periphery 162 of the lower reflective surface 138 along a path parallel to central axis X, and from the outermost periphery of the lower reflective surface through the upper central orifice 124 to the image sensor 158.

The upper reflective surface 122 is shaped to receive a minimum angle of emitted radiation from the test area 18, represented by rays E and F, to contact an innermost periphery 164 of the upper reflective surface adjacent the upper central orifice 124. Since the lower reflective surface 138 is identical in shape to upper reflective surface 122, the rays E and F are also reflected to the lower reflective surface 138 at the innermost periphery 166 adjacent the lower central orifice 140, and from there through the upper central orifice 124 to the image sensor 158. Thus, with the probe 100, the location of the source of actinic radiation 154 does not obstruct the emitted radiation at the maximum angle and does not obstruct the emitted radiation at the minimum angle.

In an exemplary embodiment, the probe 100 further includes a cartridge 168 shaped to receive the source of actinic radiation 154. The cartridge 168 includes a plurality of spokes 170, in an embodiment two spokes, extending in a radial direction and attached to the cylindrical body 104. Each of the spokes 170 includes a sleeve 172 at its outer end that extends into a recess 174 formed in the body 104 and is retained therein by a screw 176 that is threaded into a shoulder 178 formed in the recess. Also in embodiments, the source of actinic radiation 154 is a source of UV light, or primarily UV light, such as a UV LED. The cartridge 168 in embodiments includes a high-pass filter 190 that passes UV radiation light but blocks radiation of other wavelengths from the UV LED 154 to prevent false reads by the image sensor 158.

A source of electrical power 180 is mounted on the cylindrical body 104 and connected to activate the source of actinic radiation 154. The source of electrical power 180 is selected from an electrical plug adapted to be connected to a source of electrical power 182, and a battery.

In an embodiment, the probe 102 includes an image sensor 158 incorporated in a digital camera 156, and is connected, either by wire or wirelessly, to an image processor 30 that includes a display 64, the entirety of which, combined with the probe 102, comprises the system 100. The image processor 30 and display 64 may take the form of a laptop computer with display, a handheld device such as a smartphone, a tablet, or a remote device or system such as a networked computing system.

The probe 102 further includes a top cover 184 attached to the cylindrical housing 104. In an embodiment, the top cover 184 has a recess 186 shaped to receive the digital camera 156, and a central opening 188 in the recess concentric with the upper central orifice 124, such that the image sensor is concentric with the central axis X.

In sum, in an exemplary embodiment, the system 100 for measuring thermal degradation of composites includes a probe 102 having a cylindrical body 104 with a top opening 106, a bottom opening 108, and a central axis X. A bottom cover 110 encloses the bottom opening and includes a lower central aperture 112 concentric with the central axis X. An upper concave mirror 120 is mounted in the cylindrical body 104 and faces the bottom cover 110, the upper concave mirror having an upper reflective surface 122 and an upper central orifice 124 concentric with the central axis X. Further, the probe 102 includes a lower concave mirror 136 mounted in the cylindrical body 102 and facing the upper concave mirror 120, the lower concave mirror having a lower reflective surface 128 and a lower central orifice 140 concentric with the central axis X. A source of actinic radiation 156 is positioned within the cylindrical body between the upper concave mirror and the lower concave mirror on the central axis to direct actinic radiation along the central axis through the lower central orifice and the lower central aperture, and a camera 156 is mounted on the cylindrical body and has an image sensor 158 positioned concentrically relative to the upper central orifice. A display 64 is connected to the camera 156 for displaying an image of radiation emitted from a test area 18 exposed to the actinic radiation and collected by the image sensor. The display 64 displays an image that is processed by image processor 30 in the manner described with reference to FIGS. 2, 3A-3C, and 4A-4C. The bottom cover 110 is adjustable relative to the cylindrical body 102 to provide a focusing function to the image on the display 64.

A method for making the probe 102 for use in measuring thermal degradation of composites in the system 100 is as follows. The source of actinic radiation 154 is inserted into the interior 118 of the cylindrical body 104 and is attached thereto by attaching the sleeves 172 of the spokes 170 to the cylindrical body by screws 176. The lower concave mirror 136 is inserted into the interior 118 of the cylindrical body 104 through the bottom opening 108 and is attached to the cylindrical body 104 by screws 152. The lower concave mirror 136 has a lower reflective surface 138 facing the source of actinic radiation 154 and a lower central orifice 140 concentric with the central axis X. The upper concave mirror 120 is inserted into the interior 118 of the cylindrical body 104 and is attached thereto by screws 134. The upper concave mirror 120 has an upper reflective surface 122 facing the lower reflective surface 138 and the source of actinic radiation 154. The upper concave mirror 120 has an upper central orifice 124 concentric with the central axis X, such that the source of actinic radiation 154 is between the upper concave mirror 120 and the lower concave mirror 136 on the central axis and is positioned to direct actinic radiation along the central axis through the lower central orifice.

A camera 156 is mounted on the cylindrical body 104 by inserting it into the recess 186 of the top cover 184 so that the image sensor 158 extends through the opening 188, and attaching the top cover to the cylindrical body 104. The image sensor 158 is positioned concentrically relative to the upper central orifice 124. The bottom cover 110 is attached to the cylindrical body 104. In embodiments, the bottom cover is threaded onto the cylindrical body. The bottom cover 110 encloses the bottom opening 108 and includes a lower central aperture 112 concentric with the central axis X. The bottom cover 110 is adjustable relative to the cylindrical body 104 to provide a focusing function to the emitted radiation received by the image sensor 158 by varying a distance from the lower central orifice 112 and the upper reflective surface 122.

To operate the system 100, the probe 102 is grasped by the hand of a user, or in embodiments is attached to a movable extension arm, and is placed on the composite 20 to be tested, so that the bottom cover 114 rests flat upon the upper surface 116 of the composite and the lower central aperture 112 is over the test area 18. The source of actinic radiation 154, which in embodiments is a UV-LED light source receiving power from the power source 180. The power source 180 may be a power plug connected to a source of electric power 182, or itself may be a battery. The source of actinic radiation 154 may be switched on at this time, or already may be activated.

Ultraviolet actinic radiation is directed from the source 154 to project radiation 50 directly along the axis X through the lower central orifice 140 of the lower mirror 136 and the lower central aperture 112 to irradiate the test area 18 of the composite 20. Cracks and other discontinuities that may be present in the test area 18 react to UV irradiation by fluorescing emitted radiation in the visible light range. The emitted radiation 28 from the test area 18, which is bounded by rays C and D on the outside or widest angle, and rays E and F on the inside or widest angle, which extend 360° about axis A, travel directly to upper reflective surface 122 of upper mirror 120.

The rays are reflected from the upper reflective surface 122 to the lower reflective surface 138 of the lower mirror 136. Because the upper reflective surface 122 is parabolic in shape, the rays are reflected from it in a direction parallel to the central axis X. The lower reflective surface 138 receives the parallel rays from the upper reflective surface 122 and, because of its parabolic shape, reflect them in a conical volume defined by outer rays C and D and inner rays E and F through the upper central orifice 124 to converge on the image sensor 158 of the camera 156. The image of the test area 18, which may include areas of emitted radiation in the visible light range, is transmitted to image processor 30 and display 64, which function to process the image as previously described with reference to FIGS. 2, 3A-3C, and 4A-4C. Focusing of the image of the test surface 18 is effected by rotation of the bottom cover 110 relative to the body 102, which lifts or lowers the body relative to the composite surface 116, thereby lengthening or shortening the light path from the test area 18 to the image sensor 158.

The system 100 thus provides a compact probe 102 that is robust, easily adjustable, and relatively inexpensive to fabricate, assemble, and replace components. The adjustable feature provided by the bottom cover 110 may be done on the fly during the taking of a measurement. The system also is relatively simple to use and therefore may be employed by a relatively unskilled operator.

While the systems and methods for measuring thermal degradation of composites described herein constitute preferred embodiments of the method and system, the scope of the disclosure is not limited to these precise methods and systems, and changes may be made therein without departing from the scope of the appended claims.

What is claimed is:

1. A probe for use in measuring thermal degradation of composites, the probe comprising:
   a cylindrical body having a top opening, a bottom opening, and a central axis;
   a bottom cover enclosing the bottom opening and including a lower central aperture concentric with the central axis;
   an upper mirror mounted in the cylindrical body and facing the bottom cover, the upper mirror having an upper concave reflective surface and an upper central orifice concentric with the central axis;
   a lower mirror mounted in the cylindrical body and facing the upper concave reflective surface, the lower mirror having a lower concave reflective surface and a lower central orifice concentric with the central axis;
   a source of actinic radiation positioned within the cylindrical body between the upper mirror and the lower mirror on the central axis to direct actinic radiation along the central axis through the lower central orifice and the lower central aperture to a test area visible through the lower central aperture; and
   a camera mounted on the cylindrical body and having an image sensor positioned concentrically relative to the upper central orifice to receive radiation emitted from the test area in response to exposure to the actinic radiation;
   wherein the bottom cover is adjustable relative to the cylindrical body to provide a focusing function to the emitted radiation reflected from the lower reflective surface received by the image sensor by varying a distance from the lower central orifice and the upper reflective surface.

2. The probe of claim 1, wherein the bottom cover is threaded onto the cylindrical body, such that rotation of the bottom cover relative to the cylindrical body moves the bottom cover toward and away from the cylindrical body, thereby providing the focusing function.

3. The probe of claim 1, wherein the upper reflective surface and the lower reflective surface are coaxial with the cylindrical body.

4. The probe of claim 1, wherein the upper reflective surface and the lower reflective surface are paraboloid in shape.

5. The probe of claim 4, wherein the upper reflective surface and the lower reflective surface have identical paraboloid curvatures.

6. The probe of claim 1, wherein the upper central orifice and the lower central orifice are equal in diameter.

7. The probe of claim 6, wherein the source of actinic radiation is positioned within the cylindrical body between the upper reflective surface and the lower reflective surface in a location that does not block emitted radiation from the source of actinic radiation that passes from a test area through the central aperture to the upper reflective surface.

8. The probe of claim 7, wherein the source of actinic radiation is positioned within the cylindrical body between the upper reflective surface and the lower reflective surface in a location that does not block the emitted radiation from the source of actinic radiation that is reflected from the lower reflective surface to the image sensor.

9. The probe of claim 8, wherein the source of actinic radiation is positioned within the cylindrical body between the upper reflective surface and the lower reflective surface in a location that does not block emitted radiation from the source of actinic radiation that is reflected through the central aperture to the upper reflective surface, and that does not block emitted radiation from the source of actinic radiation that is reflected from the lower reflective surface to the image sensor.

10. The probe of claim 6, wherein the lower central orifice is shaped such that a maximum angle of emitted radiation from a test area passing therethrough contacts an outermost periphery of the upper reflective surface, and is reflected to an outermost periphery of the lower reflective surface, and from the outermost periphery of the lower reflective surface through the upper central orifice to the image sensor.

11. The probe of claim 10, wherein the upper reflective surface is shaped to receive a minimum angle of emitted radiation from the test area to contact an innermost periphery of the upper reflective surface adjacent the upper central orifice.

12. The probe of claim 11, wherein the source of actinic radiation does not obstruct the emitted radiation at the maximum angle and does not obstruct the emitted radiation at the minimum angle.

13. The probe of claim 1, further comprising a cartridge shaped to receive the source of actinic radiation, the cartridge including a plurality of spokes extending in a radial direction and attached to the cylindrical body.

14. The probe of claim 13, wherein the source of actinic radiation is an ultraviolet light emitting diode.

15. The probe of claim 1, further comprising a source of electrical power mounted on the cylindrical body and connected to activate the source of actinic radiation.

16. The probe of claim 15, wherein the source of electrical power is selected from an electrical plug adapted to be connected to a source of electrical power, and a battery.

17. The probe of claim 1, wherein the image sensor is incorporated in a digital camera.

18. The probe of claim 17, further comprising a top cover attached to the cylindrical housing, the top cover having a recess shaped to receive the digital camera, and a central opening in the recess concentric with the upper central orifice, such that the image sensor is concentric with the central axis.

19. A system for measuring thermal degradation of composites, the system comprising:
a probe having
a cylindrical body having a top opening, a bottom opening, and a central axis;
a bottom cover enclosing the bottom opening and including a lower central aperture concentric with the central axis;
an upper concave mirror mounted in the cylindrical body and facing the bottom cover, the upper concave mirror having an upper reflective surface and an upper central orifice concentric with the central axis;
a lower concave mirror mounted in the cylindrical body and facing the upper concave mirror, the lower concave mirror having a lower reflective surface and a lower central orifice concentric with the central axis;
a source of actinic radiation positioned within the cylindrical body between the upper concave mirror and the lower concave mirror on the central axis and positioned to direct actinic radiation along the central axis through the lower central orifice and the lower central aperture; and
a camera mounted on the cylindrical body and having an image sensor positioned concentrically relative to the upper central orifice; and
a display connected to the camera for displaying an image of radiation emitted from a test area exposed to the actinic radiation and collected by the image sensor;
wherein the bottom cover is adjustable relative to the cylindrical body to provide a focusing function to the image on the display.

20. A method for making a probe for use in measuring thermal degradation of composites, the method comprising:
mounting a source of actinic radiation within a cylindrical body, the cylindrical body having a bottom opening and a central axis;
attaching a lower concave mirror to the cylindrical body, the lower concave mirror having a lower reflective surface facing the source of actinic radiation and a lower central orifice concentric with the central axis;
mounting an upper concave mirror in the cylindrical body, the upper concave mirror having an upper reflective surface facing the lower reflective surface and the source of actinic radiation, the upper concave mirror having an upper central orifice concentric with the central axis, such that the source of actinic radiation is between the upper concave mirror and the lower concave mirror on the central axis and positioned to direct actinic radiation along the central axis through the lower central orifice;
mounting a camera on the cylindrical body, the camera having an image sensor positioned concentrically relative to the upper central orifice; and
attaching a bottom cover to the cylindrical body, the bottom cover enclosing the bottom opening and including a lower central aperture concentric with the central axis;
wherein the bottom cover is adjustable relative to the cylindrical body to provide a focusing function to the emitted radiation received by the image sensor by varying a distance from the lower central orifice and the upper reflective surface.

* * * * *